(12) United States Patent
Bly et al.

(10) Patent No.: US 7,949,409 B2
(45) Date of Patent: May 24, 2011

(54) DUAL SPIRAL LEAD CONFIGURATIONS

(75) Inventors: Mark J. Bly, Falcon Heights, MN (US);
Anthony V. Caparso, St. Louis Park, MN (US); Randy W. Westlund, River Falls, WI (US); Ronald W. Heil, Jr., Roseville, MN (US); Brendan E. Koop, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 194 days.

(21) Appl. No.: 11/668,887

(22) Filed: Jan. 30, 2007

(65) Prior Publication Data

US 2008/0183254 A1    Jul. 31, 2008

(51) Int. Cl.
*A61N 1/00* (2006.01)
*A61B 18/04* (2006.01)

(52) U.S. Cl. ........ 607/116; 607/115; 607/127; 607/131; 606/32

(58) Field of Classification Search .................. 607/115, 607/127, 131
See application file for complete search history.

(56) References Cited

U.S. PATENT DOCUMENTS

| | | | |
|---|---|---|---|
| 4,365,634 A | 12/1982 | Bare et al. | |
| 4,414,986 A | 11/1983 | Dickhudt et al. | |
| 4,774,949 A | 10/1988 | Fogarty | |
| 4,905,667 A | 3/1990 | Foerster et al. | |
| 4,920,979 A | 5/1990 | Bullara | |
| 4,944,088 A | 7/1990 | Doan et al. | |
| 5,016,808 A | 5/1991 | Heil, Jr. et al. | |
| 5,221,261 A | 6/1993 | Termin et al. | |
| 5,265,608 A | 11/1993 | Lee et al. | |
| 5,330,515 A | 7/1994 | Rutecki et al. | |
| 5,351,394 A * | 10/1994 | Weinberg ........................ | 29/872 |
| 5,378,239 A | 1/1995 | Termin et al. | |
| 5,383,922 A | 1/1995 | Zipes et al. | |
| 5,387,233 A | 2/1995 | Alferness et al. | |
| 5,411,546 A | 5/1995 | Bowald et al. | |
| 5,423,865 A * | 6/1995 | Bowald et al. .................... | 607/5 |
| 5,476,498 A | 12/1995 | Ayers | |
| 5,496,277 A | 3/1996 | Termin et al. | |
| 5,531,779 A | 7/1996 | Dahl et al. | |
| 5,540,730 A | 7/1996 | Terry, Jr. et al. | |
| 5,755,714 A | 5/1998 | Murphy-Chutorian | |
| 5,755,761 A | 5/1998 | Obino | |

(Continued)

FOREIGN PATENT DOCUMENTS

DE    10103288    8/2002

(Continued)

OTHER PUBLICATIONS

International Search Report and Written Opinion of international application No. PCT/US2007/086119, mailed Apr. 3, 2007, 15 pp.

(Continued)

*Primary Examiner* — Niketa I Patel
*Assistant Examiner* — Nicole F Lavert
(74) *Attorney, Agent, or Firm* — Faegre & Benson LLP (57) ABSTRACT

A medical electrical lead for transvascularly stimulating a nerve, muscle or other tissue from an adjacent vessel is described. The lead includes a bifurcated distal portion including a first elongate member forming a first spiral and a second elongate member forming a second spiral. The spirals can be in parallel or serial alignment with one another.

24 Claims, 7 Drawing Sheets

U.S. PATENT DOCUMENTS

| | | | |
|---|---|---|---|
| 5,766,203 | A | 6/1998 | Imran et al. |
| 5,772,693 | A | 6/1998 | Brownlee |
| 5,792,187 | A | 8/1998 | Adams |
| 5,803,928 | A | 9/1998 | Tockman et al. |
| 5,871,531 | A | 2/1999 | Struble |
| 5,954,761 | A | 9/1999 | Machek et al. |
| 5,997,536 | A | 12/1999 | Osswald et al. |
| 6,006,134 | A | 12/1999 | Hill et al. |
| 6,021,354 | A | 2/2000 | Warman et al. |
| 6,055,456 | A | 4/2000 | Gerber |
| 6,292,695 | B1 | 9/2001 | Webster, Jr. et al. |
| 6,321,123 | B1 | 11/2001 | Morris et al. |
| 6,363,288 | B1 | 3/2002 | Bush et al. |
| 6,385,492 | B1 | 5/2002 | Ollivier et al. |
| 6,397,109 | B1 | 5/2002 | Cammilli et al. |
| 6,429,217 | B1 | 8/2002 | Puskas |
| 6,442,413 | B1 | 8/2002 | Silver |
| 6,449,507 | B1 | 9/2002 | Hill et al. |
| 6,516,232 | B2 | 2/2003 | Skinner |
| 6,564,096 | B2 | 5/2003 | Mest |
| 6,584,362 | B1 | 6/2003 | Scheiner et al. |
| 6,600,956 | B2 | 7/2003 | Maschino et al. |
| 6,656,960 | B2 | 12/2003 | Puskas |
| 6,671,562 | B2 | 12/2003 | Osypka et al. |
| 6,704,604 | B2 | 3/2004 | Soukup et al. |
| 6,760,626 | B1 * | 7/2004 | Boveja ............... 607/59 |
| 6,766,203 | B2 | 7/2004 | Doan et al. |
| 6,778,854 | B2 | 8/2004 | Puskas |
| RE38,654 | E | 11/2004 | Hill et al. |
| RE38,705 | E | 2/2005 | Hill et al. |
| 6,882,887 | B1 * | 4/2005 | Shelchuk et al. ............ 607/122 |
| 6,889,092 | B2 | 5/2005 | Zhu et al. |
| 6,901,297 | B2 | 5/2005 | Frericks et al. |
| 6,934,583 | B2 | 8/2005 | Weinberg et al. |
| 6,934,589 | B2 | 8/2005 | Sundquist et al. |
| 6,973,340 | B2 | 12/2005 | Fuimaono et al. |
| 7,047,084 | B2 | 5/2006 | Erickson et al. |
| 7,058,454 | B1 | 6/2006 | Chitre et al. |
| 7,676,275 | B1 | 3/2010 | Farazi et al. |
| 2002/0026228 | A1 | 2/2002 | Schauerte |
| 2002/0032963 | A1 | 3/2002 | Lindegren |
| 2002/0087192 | A1 | 7/2002 | Barrett et al. |
| 2002/0151949 | A1 | 10/2002 | Dahl et al. |
| 2002/0183237 | A1 | 12/2002 | Puskas |
| 2002/0183817 | A1 | 12/2002 | Van Venrooij et al. |
| 2002/0198570 | A1 | 12/2002 | Puskas |
| 2002/0198571 | A1 | 12/2002 | Puskas |
| 2003/0074039 | A1 | 4/2003 | Puskas |
| 2003/0078623 | A1 | 4/2003 | Weinberg et al. |
| 2003/0105506 | A1 | 6/2003 | Krishnan et al. |
| 2003/0195506 | A1 * | 10/2003 | Stewart et al. ............... 606/41 |
| 2003/0195603 | A1 | 10/2003 | Scheiner et al. |
| 2003/0199961 | A1 | 10/2003 | Bjorklund et al. |
| 2003/0229380 | A1 | 12/2003 | Adams et al. |
| 2004/0015204 | A1 | 1/2004 | Whitehurst et al. |
| 2004/0015205 | A1 | 1/2004 | Whitehurst et al. |
| 2004/0019359 | A1 | 1/2004 | Worley et al. |
| 2004/0019377 | A1 | 1/2004 | Taylor et al. |
| 2004/0030362 | A1 | 2/2004 | Hill et al. |
| 2004/0059383 | A1 | 3/2004 | Puskas |
| 2004/0059404 | A1 | 3/2004 | Bjorklund et al. |
| 2004/0062852 | A1 | 4/2004 | Schroeder et al. |
| 2004/0133240 | A1 | 7/2004 | Adams et al. |
| 2004/0147825 | A1 | 7/2004 | Milojevic et al. |
| 2004/0172075 | A1 | 9/2004 | Shafer et al. |
| 2004/0172088 | A1 | 9/2004 | Knudson et al. |
| 2004/0176782 | A1 | 9/2004 | Hanse et al. |
| 2004/0186531 | A1 | 9/2004 | Jahns et al. |
| 2004/0260374 | A1 | 12/2004 | Zhang et al. |
| 2005/0021119 | A1 | 1/2005 | Sage et al. |
| 2005/0038489 | A1 | 2/2005 | Grill |
| 2005/0060015 | A1 | 3/2005 | Tanaka |
| 2005/0065553 | A1 | 3/2005 | Ben Ezra et al. |
| 2005/0080472 | A1 | 4/2005 | Atkinson et al. |
| 2005/0113862 | A1 | 5/2005 | Besselink et al. |
| 2005/0131467 | A1 | 6/2005 | Boveja |
| 2005/0143412 | A1 | 6/2005 | Puskas |
| 2005/0149126 | A1 | 7/2005 | Libbus |
| 2005/0149155 | A1 | 7/2005 | Scheiner et al. |
| 2005/0197675 | A1 | 9/2005 | David et al. |
| 2005/0251239 | A1 | 11/2005 | Wallace et al. |
| 2006/0206153 | A1 | 9/2006 | Libbus et al. |
| 2006/0229677 | A1 | 10/2006 | Moffitt et al. |
| 2006/0241737 | A1 | 10/2006 | Tockman et al. |
| 2006/0259085 | A1 | 11/2006 | Zhang et al. |
| 2006/0259107 | A1 | 11/2006 | Caparso et al. |
| 2008/0051861 | A1 * | 2/2008 | Cross et al. ............... 607/116 |
| 2008/0183186 | A1 | 7/2008 | Bly et al. |
| 2008/0183187 | A1 | 7/2008 | Bly |
| 2008/0183253 | A1 | 7/2008 | Bly |
| 2008/0183255 | A1 | 7/2008 | Bly et al. |
| 2008/0183259 | A1 | 7/2008 | Bly et al. |
| 2008/0183264 | A1 | 7/2008 | Bly et al. |
| 2008/0183265 | A1 | 7/2008 | Bly et al. |
| 2009/0171425 | A1 | 7/2009 | Dahlberg |

FOREIGN PATENT DOCUMENTS

| | | |
|---|---|---|
| EP | 045317 | 10/1991 |
| EP | 453117 | 10/1991 |
| EP | 0795343 | 9/1997 |
| EP | 1304135 | 4/2003 |
| JP | 05049701 A | 3/1993 |
| WO | 8304181 | 12/1983 |
| WO | 9956817 | 11/1999 |
| WO | 0100273 A1 | 1/2001 |
| WO | 0218006 | 3/2002 |
| WO | 2006098996 | 9/2006 |

OTHER PUBLICATIONS

Nabutovsky et al., "Lead Design and Initial Applications of a New Lead for Long-Term Endovascular Vagal Stimulation," PACE, vol. 30, Jan. 2007 Supplement 1, pp. S215-S218.

Web Site, Guidant Fineline II Sterox and Fineline II Sterox EZ, http://www/guidant.com/productstemplates/crm/fineline_II_sterox.shtml.

Tarver et al., "Clinical Experience with a Helical Bipolar Stimulating Lead," PACE, October, Part II 1992, pp. 1545-1556, vol. 15, Cyberonics, Inc., Webster, Texas and the Department of Neurosurgery, Baylor College of Medicine.

Li et al., "Vagal Nerve Stimulation Markedly Improves Long-Term Survival After Chronic Heart Failure in Rats," Circulation Journal of the American Heart Association, Dec. 8, 2003, pp. 120-124.

* cited by examiner

Fig. 7B

DUAL SPIRAL LEAD CONFIGURATIONS

CROSS-REFERENCE TO RELATED APPLICATION

This application is related to the following and co-owned applications entitled: SPIRAL LEAD CONFIGURATIONS FOR INTRAVASCULAR LEAD STABILITY, filed on Jan. 30, 2007 and assigned Ser. No. 11/668,926, now published application No. U.S. 2008/0183259; ELECTRODE CONFIGURATIONS FOR TRANSVASCULAR NERVE STIMULATION, filed on Jan. 30, 2007 and assigned Ser. No. 11.668,957, now published application No. U.S. 2008/0183264; TRANSVASCULAR LEAD WITH PROXIMAL FORCE RELIEF, filed on Jan. 30, 2007 and assigned Ser. No. 11/669,039, now published application No. U.S. 2008/0183265; METHOD AND APPARATUS FOR DELIVERING A TRANSVASCULAR LEAD, filed on Jan. 30, 2007 and assigned Ser. No. 11/669,042, now published application No. U.S. 2008/0183186; DIRECT DELIVERY FOR TRANSVASCULAR LEAD, filed on Jan. 30, 2007 and assigned Ser. No. 11/669,047, now published application No. U.S. 2008/0183187; SIDE PORT LEAD DELIVERY SYSTEM, filed on Jan. 30, 2007 and assigned Ser. No. 11/669,050, now published application No. U.S. 2008/0183255; and NEUROSTIMULATING LEAD HAVING A STENT-LIKE ANCHOR, filed on Jan. 30, 2007 and assigned Ser. No. 11/668,834, now published application No. U.S. 2008/0183253, all of which are herein incorporated by reference.

TECHNICAL FIELD

The present invention relates to medical electrical leads for nerve or muscle stimulation and their configurations. More specifically, the present invention relates to medical electrical lead configurations for stabilizing leads in an intravascular location adjacent a nerve to be stimulated.

BACKGROUND

A significant amount of research has been directed both to the direct and indirect stimulation of nerves including the left and right vagus nerves, the sympathetic and parasympathetic nerves, the phrenic nerve, the sacral nerve, and the cavernous nerve to treat a wide variety of medical, psychiatric, and neurological disorders or conditions. More recently, stimulation of the vagus nerve has been proposed as a method for treating various heart conditions, including heart failure.

Typically in the past, nerve stimulating electrodes were cuffs placed in direct contact with the nerve to be stimulated. A much less invasive approach is to stimulate the nerve through an adjacent vein using an intravascular lead. A lead including one or more electrodes is inserted into a patient's vasculature and delivered at a site within a vessel adjacent a nerve to be stimulated. However, without any additional means of stabilizing the lead within the vein, the lead can move and/or rotate causing the electrodes to migrate from the stimulation site.

Thus, it is desirable to develop a mechanism to minimize lead rotation and movement and allow for chronic therapy to be reliably delivered.

SUMMARY

According to one embodiment of the present invention, an intravascular lead adapted to be deployed to a stimulation site within a vessel adjacent a nerve or muscle to be stimulated includes: a lead body including a proximal end adapted to be connected to a pulse generator; a bifurcated distal portion having at least a first elongated member forming a first spiral and a second elongated member forming a second spiral; and one or more electrodes located on the distal portion. The distal portion is adapted to transition from a collapsed configuration to an expanded configuration. In the expanded configuration, a least one spiral is adapted to frictionally engage a vessel wall of the vessel in which the lead is deployed. Additionally, at least one electrode is adapted to deliver an electrical pulse transvascularly to the nerve or muscle to be stimulated. According to a further embodiment of the present invention the first and second spirals are anti-parallel, congruent spirals having the same longitudinal axis forming a double helix.

According to another embodiment of the present invention, an intravascular lead adapted to be deployed to a stimulation site within a vessel adjacent a nerve or muscle to be stimulated includes: a lead body including a proximal end adapted to be connected to a pulse generator and a bifurcated distal portion. The distal portion includes at least a first elongated member forming a first spiral and a second elongated member forming a second spiral. According to a further embodiment of the present invention, the lead includes one or more electrodes located on at least one spiral. At least one electrode is adapted to deliver an electrical pulse transvascularly to the nerve or muscle to be stimulated.

According to yet another embodiment, the present invention is a method of providing a therapy to a nerve or muscle from within an adjacent vessel using an intravascular medical lead including a lead body having a proximal end connected to a pulse generator and a bifurcated distal portion having at least a first elongated member forming a first spiral and a second elongated member forming a second spiral. The method includes collapsing the distal portion to its collapsed configuration; delivering the distal portion of the lead to a stimulation site located within an adjacent vessel; and stimulating the adjacent nerve or muscle. According to a further embodiment, the method also includes detecting an optimal stimulation threshold.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

While the embodiments described herein generally refer to placement of a lead into the right internal jugular vein through the right or left subclavian vein, the various embodiments of the present invention as described below can be practiced at numerous sites within a patient's vasculature system. Any intravascular site that is adjacent to a nerve, muscle, or brain tissue that has the potential to benefit from stimulation is a potential site for stimulation. The term "vessel" includes all veins and arteries of the circulatory system. Additionally, the term "vessel" includes various structures of the lymphatic system, including lymph nodes, ducts, capillaries, and vessels. Likewise, as used herein, the term "vessel" also includes the various tube-like structures of the gastrointestinal system. The terms "nerve" and "nerve fiber" as used herein include a single neuron, nerve, nerve ending(s), or nerve bundle. The term "intravascular" means within the venous or arterial circulatory system, including vessels of all types and descriptions. When referring to "intravascular stimulation" in describing the embodiments of the present invention, it is meant to refer to stimulation from within the circulatory system resulting in (transvascular) stimulation of a nerve, muscle, or tissue of interest. The term "transvascular" means across a vessel or vessel wall. "Stimulation" means a stimulus, usually electrical, which causes depolarization of a cell or cells, or portion of a cell, contraction, excitation as measured by e.g., calcium or sodium influx into the cell, or an altered membrane potential across a cell.

Vessels having sufficient diameter for catheter access which are known to have nerves running adjacent to or nearby are suitable candidates for potential stimulation sites. Exemplary sites include, but are not limited to, the following: the left and right internal jugular veins, the azygous vein, the brachiocephalic (innominate) vein, the subclavian vein, the superior vena cava, the pulmonary artery, and cardiac branch vessels. Other potential stimulation sites include, but are not limited to, the following: thoracic duct, the bile duct, and sites along the upper gastrointestinal and lower gastrointestinal tracts. Exemplary nerves to be stimulated include, but are not limited to, the following: the left and right vagus nerves, the phrenic nerve, the parasympathetic nerves, the sympathetic nerves, and the sacral nerve.

Figure 1:
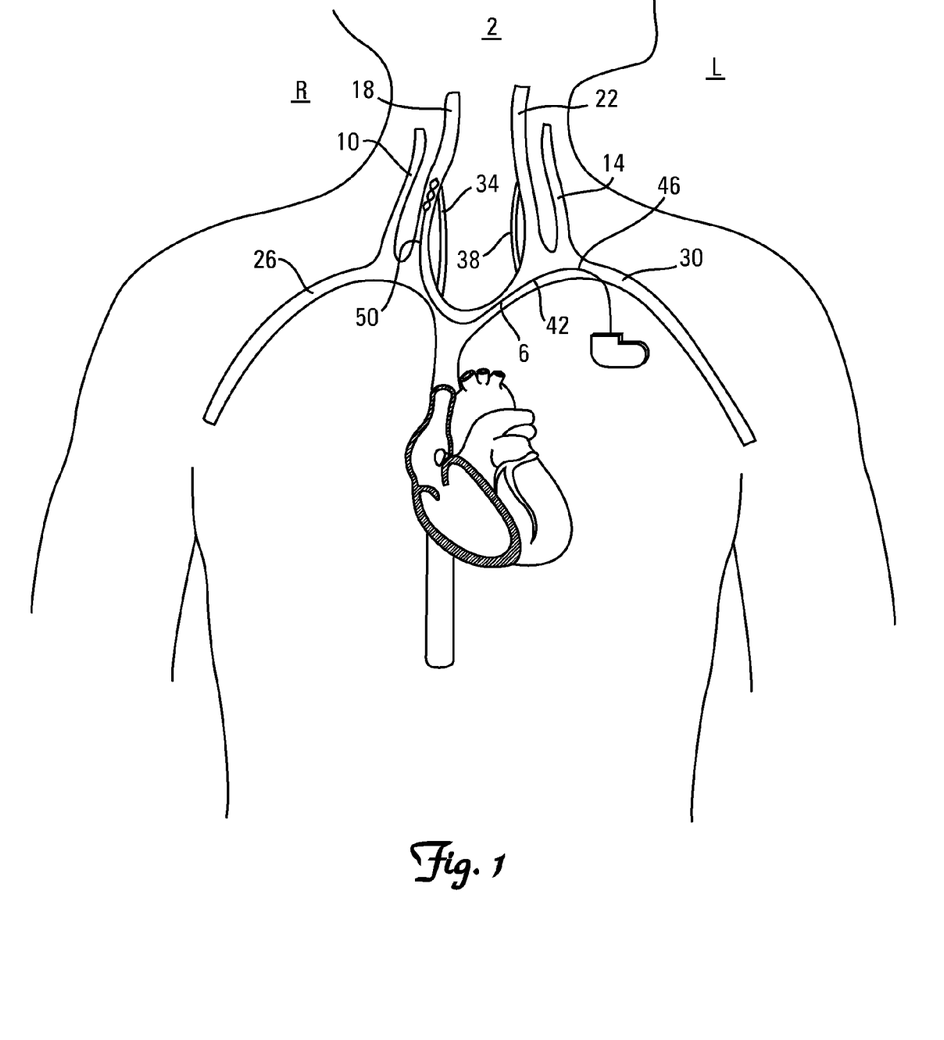
FIG. 1 is a schematic view of a lead deployed in a patient's internal jugular vein at a location adjacent the vagus nerve according to an embodiment of the present invention.
Figure 2:
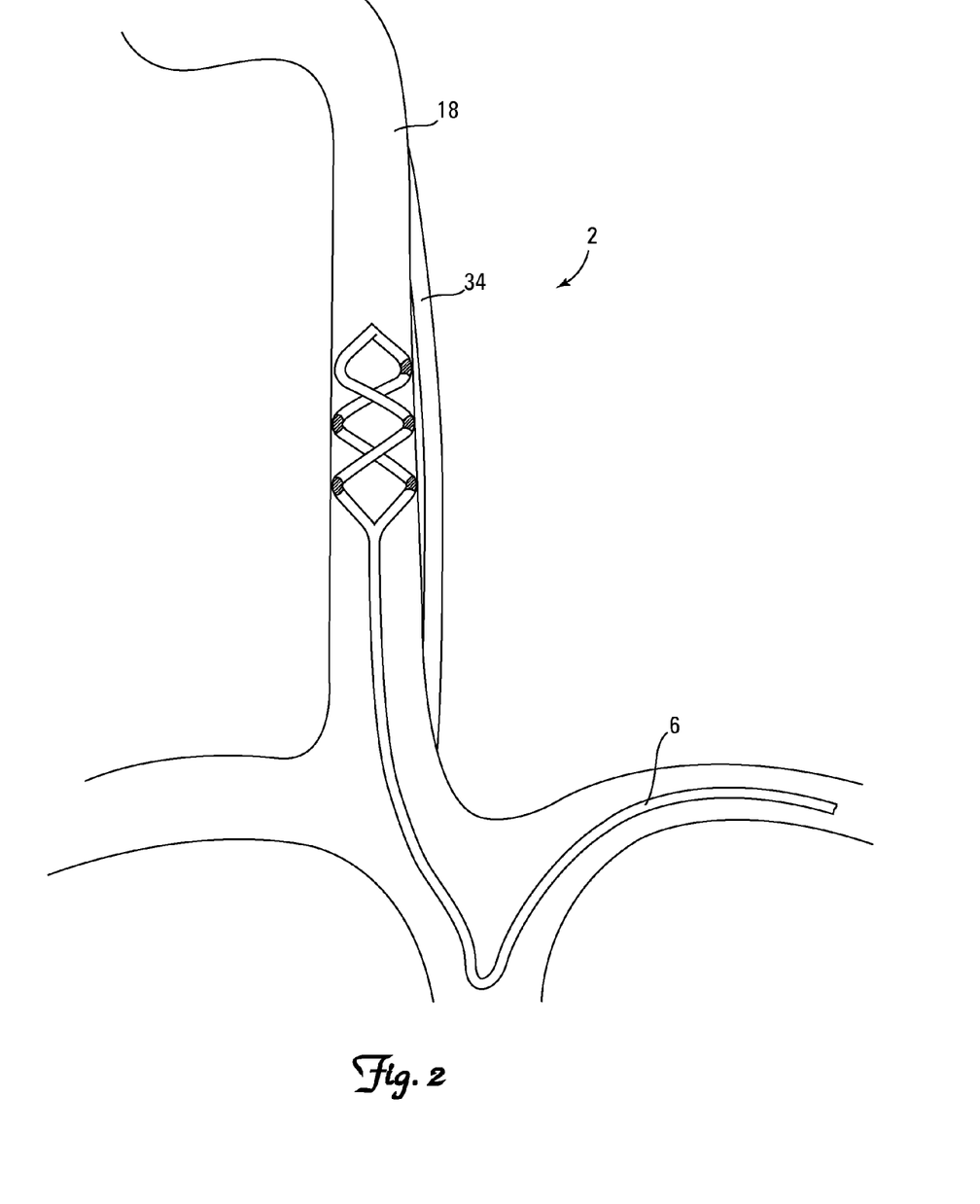
FIG. 2 is a close-up, schematic view of a lead deployed in a patient's internal jugular vein as shown in FIG. 1 according to an embodiment of the present invention.

FIG. 1 shows a perspective view of a patient's vascular system 2 including a lead 6 deployed within the system 2. FIG. 2 is a close up schematic view of the lead 6 deployed within the system 2. In general, the vascular system 2, as shown, includes the right and left external jugular veins 10 and 14, the right and left internal jugular veins 18 and 22, the right and left subclavian veins 26 and 30, portions of which are generally aligned with the right and left vagus nerves 34 and 38. As shown in FIGS. 1 and 2, the lead 6 is inserted into a patient's vasculature system through the left subclavian vein 30 and into the right internal jugular vein 18. The lead 6 is positioned in the right internal jugular vein 18 adjacent to the right vagus nerve 34. Alternatively, the lead 6 can be inserted and advanced into the vasculature system via the right subclavian vein 26.

Figure 3:
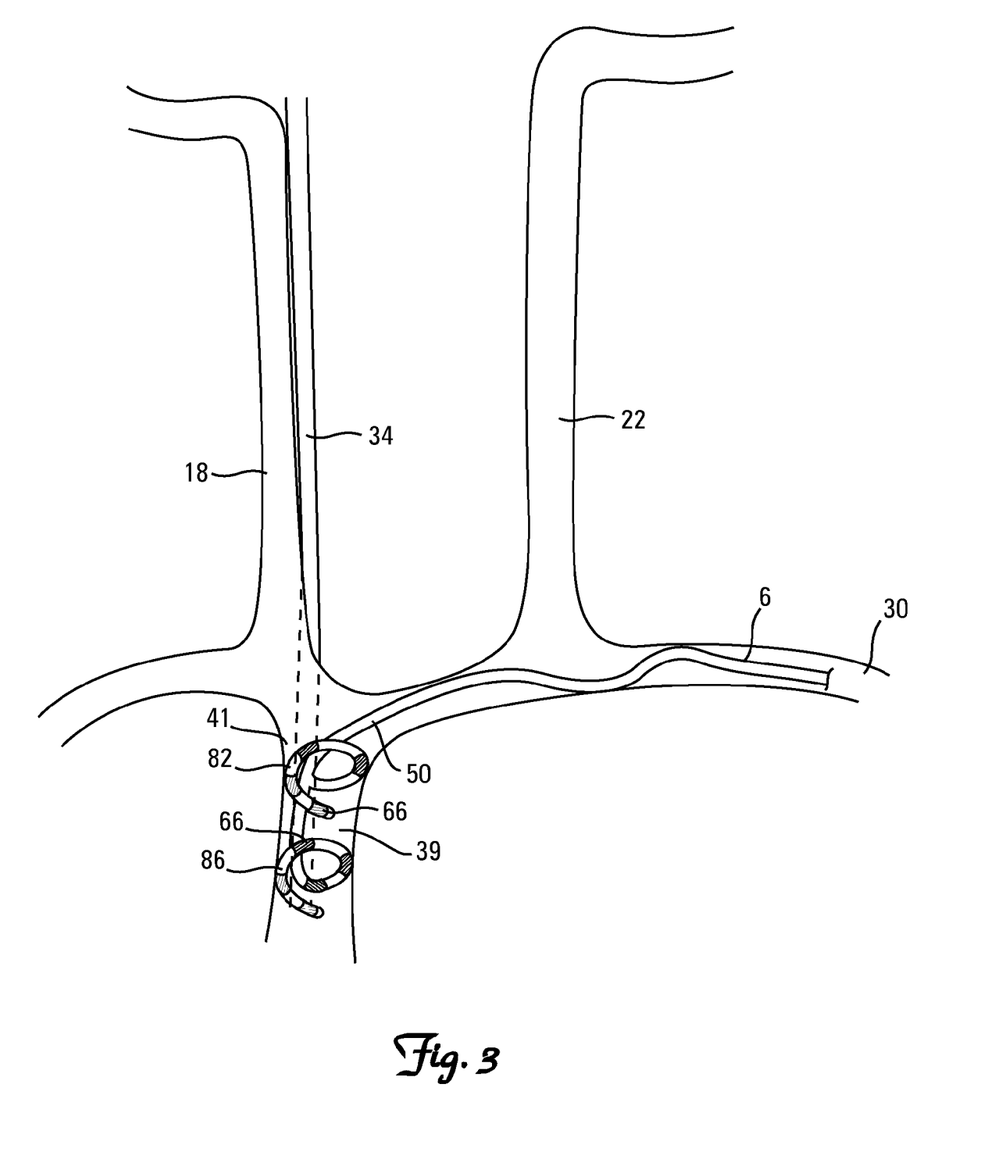
FIG. 3 is a close-up schematic view of a lead according to an embodiment of the present invention deployed in the superior vena cava.
Figure 4:
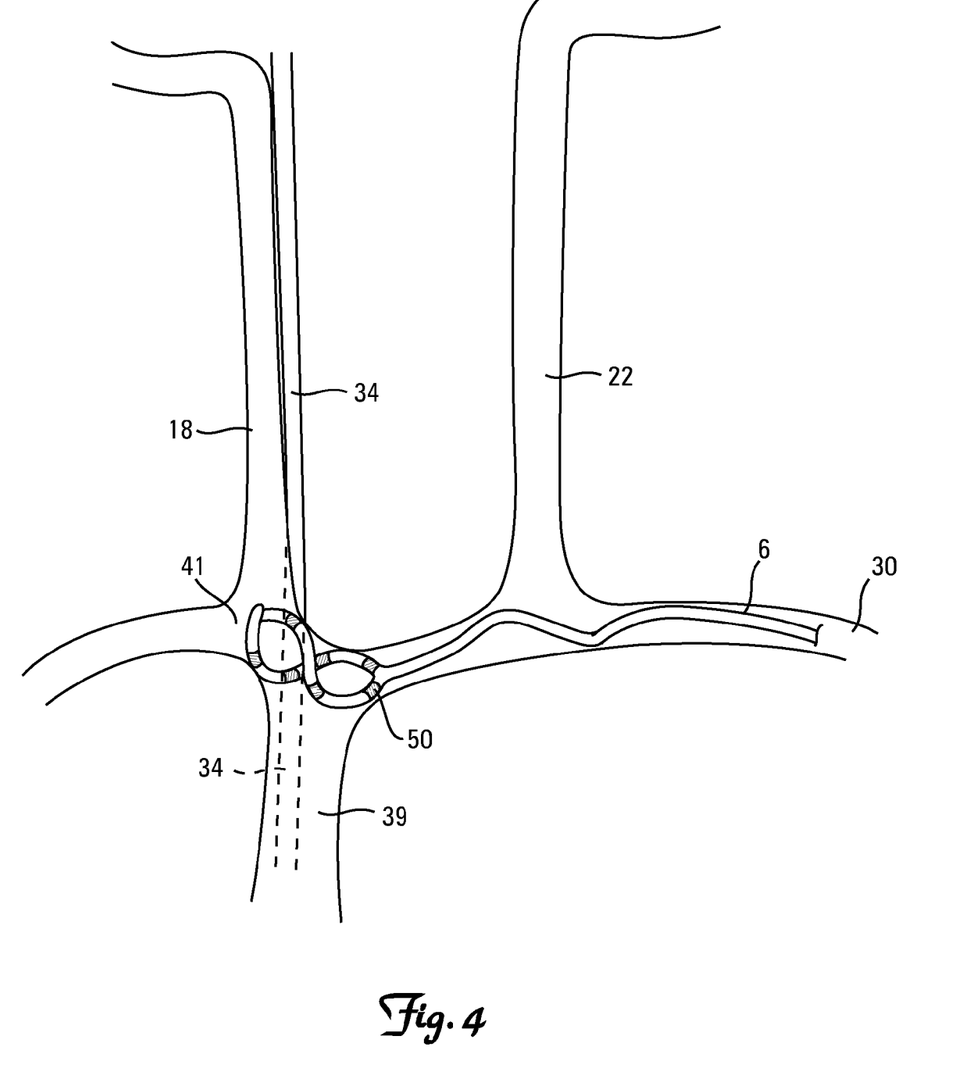
FIG. 4 is a close-up schematic view of a lead according to another embodiment of the present invention deployed in the brachiocephalic vein.

FIGS. 3 and 4 show the lead 6 deployed within alternative locations in a patient's vasculature for stimulating the vagus nerve 34. According to one embodiment, as shown in FIG. 3, the lead 6 is inserted through the right subclavian vein 30 deployed and secured in the superior vena cava 39. The portion of the vagus nerve 34 adjacent to the superior vena cava 39 is represented by the dashed lines in FIG. 3. According to another embodiment, as shown in FIG. 4, the lead 6 is inserted through the right subclavian vein 30 deployed and secured in the brachiocephalic vein 41. The portion of the vagus nerve 34 adjacent to the brachiocephalic vein 41 is represented by the dashed lines in FIG. 4.

Figure 5:
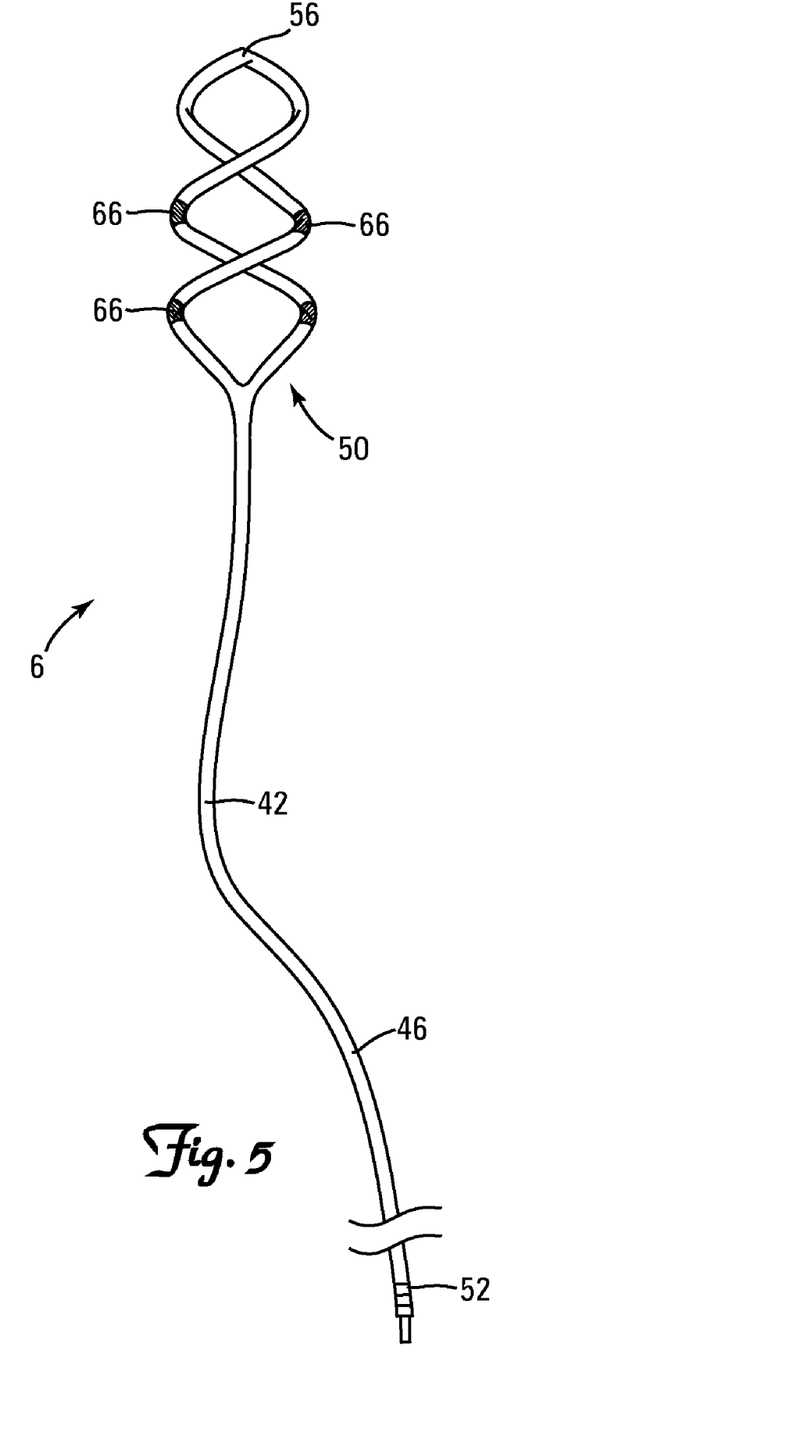
FIG. 5 is a perspective view of a lead according to an embodiment of the present invention.

FIG. 5 is a perspective view of a lead 6 according to an embodiment of the present invention. As shown in FIG. 5, the lead 6 includes a lead body 42 including a proximal portion 46 and a distal portion 50 including one or more electrodes 66. One or more electrodes 66 are positioned along the lead body 42. Additionally, the lead 6 includes a proximal end 52 adapted to be connected to a pulse generator or other implantable medical device. The lead body 42 is flexible, but substantially non-compressible along its length.

According to one embodiment of the present invention, the lead body 42 includes a plurality of conductors including individual wires, coils, or cables. These wires can be insulated conductive wires and/or molded in place with an insulator such as silicone, polyurethane, ethylene tetrafluoroethylene, or another biocompatible, insulative polymer. In one embodiment of the present invention, the lead body 42 has a co-radial design. In this embodiment, each individual conductor can be a coil including an insulative tubing. The insulated coils are then wound together in parallel to form a single coil. Alternatively, the lead body 42 is co-axial. According to a further embodiment of the present invention, each conductor is adapted to connect to an individual electrode 66 in a one-to-one manner allowing each electrode 66 to be individually addressable. In yet a further embodiment of the present invention, the lead body 42 includes a lumen adapted to receive a guiding element such as a guidewire or a stylet.

FIGS. 6A-6E show the distal portion 50 of the lead 6 according to various embodiments of the present invention. As shown in FIGS. 6A-6E, the distal portion 50 is bifurcated at one or more bifurcation points 70 along the lead body 42. According to one embodiment, the distal portion 50 of the lead 6 is stiffer than the lead body 42 and the proximal portion 46. One exemplary embodiment of such a structure is disclosed in commonly owned and co-pending published application US 2008/0183265 entitled "TRANSVASCULAR LEAD WITH PROXIMAL FORCE RELIEF," which is herein incorporated by reference. According to another embodiment of the present invention, the distal portion 50 includes a superelastic material. Exemplary superelastic materials include Nitinol and MP35N.

The bifurcated distal portion 50 includes at least a first elongate member 72 and a second elongate member 76. The first elongate member 72 forms a first spiral 82 and the second elongate member 76 forms a second spiral 86. Multiple spirals improve stability of the distal portion 50 of the lead 6 within the vessel by placing more friction against the venous walls. Additionally, multiple spirals fill out the space within a vessel lumen to form a tube-like inner support structure, increasing the stability of the lead in the vessel and decreasing a preference for a particular orientation.

Figures 6A, 6B:
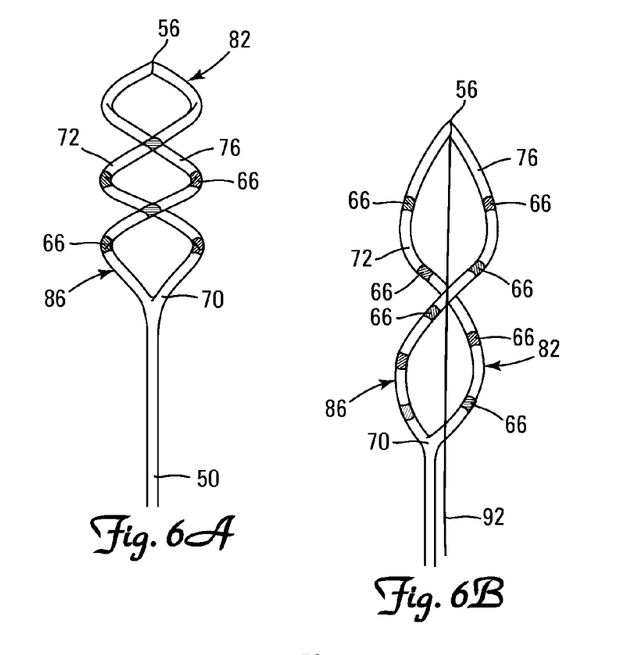
FIGS. 6A-6E show side views of a distal portion of a lead according to various embodiments of the present invention.
Figure 6C:
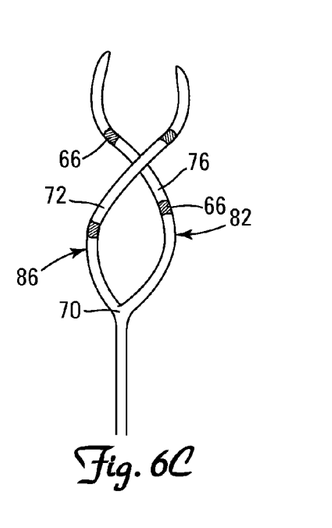

According to the embodiments shown in FIGS. 6A-6C, the spirals 82 and 86 are congruent, anti-parallel spirals having the same longitudinal axis intertwining to form a double helix. According to a further embodiment of the present invention, the elongate members 72, 76 are connected to one another at a distal end 56 of the lead 6. Alternatively, the elongate members are not attached to one another at the distal end 56 of the lead 6.

Figure 6D:
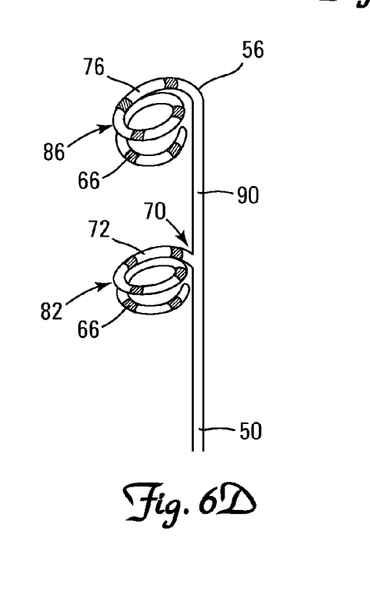
Figure 6E:
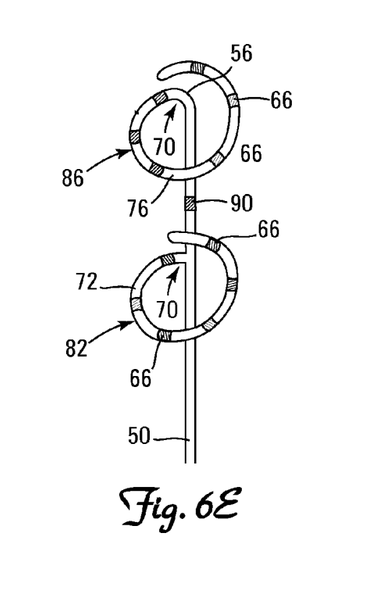

According to the embodiments shown in FIGS. 6D and 6E, the spirals 82 and 86 are in serial alignment with one another. That is, as shown in FIGS. 6D and 6E, spiral 82 is proximate to spiral 86. According to a further embodiment of the present invention, the spirals 82 and 86 are interrupted by a generally straight portion 90. The generally straight portion 90 is configured such that it runs parallel to the nerve to be stimulated. A typical length of the straight portion 90 ranges from about 1 to about 8 cm as measured from a first bifurcation point to a second bifurcation point.

The spirals 82 and 86 can wind in a clockwise or counterclockwise direction. The number of turns can range from ½ turn to multiple turns as shown in FIGS. 6A and 6D. The pitch can be described as the distance between two points on a spiral. The pitch frequency ranges from zero (lasso configuration) to 5 cm, and can remain constant or vary along the spirals 82, 86.

According to one embodiment of the present invention, the spirals 82, 86 have a predetermined effective outer diameter ranging from about 5 mm to about 50 mm. According to another embodiment of the present invention, the predetermined effective outer diameter of the spirals 82, 86 ranges from about 10 mm to about 35 mm.

The spirals 82, 86 can assume a variety of cross-sectional shapes. According to one embodiment, the spirals 82, 86 have a circular cross-sectional shape. A circular cross-sectional shape allows no bias for orientation such that when the lead is rotated within a vein the spirals 82, 86 exhibit no natural preference for a specific orientation. According to another embodiment, the spirals 82, 86 have an elliptical cross-sectional shape. The overall size, diameter and cross-sectional shape of the spirals 82, 86 can be selected depending upon the size, diameter, and shape of the vessel in which the distal portion 50 of the lead 6 is to be deployed. An overall length of each spiral 82, 86, according to an embodiment of the present invention, ranges from about 30 mm to about 200 mm depending on the anatomical demands of the patient's anatomy. More particularly, an overall length of each spiral 82, 86 can range from about 40 to about 80 mm.

According to a further embodiment of the present invention the spirals 82, 86 can increase in diameter from a proximal end of the spiral to a distal end of the spiral creating spirals 82, 86 having a predetermined shape that tapers down from a distal end of the spirals 82, 86 to a proximal end of the spirals 82, 86. Alternatively, spirals 82, 86 can have a diameter that decreases from a proximal end of spirals 82, 86 to a distal end of spirals 82, 86, creating spirals 82, 86 having a predetermined shape that tapers down from a proximal end of spirals 82, 86 towards the distal end of the spirals 82, 86.

The spirals 82, 86 are adapted to transition from a collapsed configuration to an expanded configuration. In their expanded configuration, the spirals 82, 86 have a predetermined effective diameter and are adapted to frictionally engage at least one wall of the vessel in which the distal portion 50 is deployed. According to one embodiment of the present invention, when allowed to expand within a vessel, the spirals 82, 86 will not achieve their predetermined effective diameter as the spirals 82, 86 will be constrained from fully expanding by the walls of the vessel in which they are deployed. As such the spirals 82, 86 place a radial expansion force on the walls of the vessel, providing a mechanism for stabilizing the distal portion 50 of the lead 6 in the vessel. In one exemplary embodiment, the effective outer diameter ranges from about 5 percent to about 50 percent greater than the inner diameter of the vessel in which the distal portion 50 of the lead 6 is deployed.

According to an embodiment of the present invention, one or both of the elongate members 72, 76 can include a lumen adapted to receive a guiding element such as a stylet or a guidewire adapted to assist in delivery of the distal portion 50 to a stimulation site within a vessel. Alternatively, a guide catheter is provided to deliver the distal portion 50 to a stimulation site within a vessel. The stylet, guidewire, or guide catheter, either alone or in combination with one another, is used to collapse (either fully or partially) the distal portion 50 including the spirals 82, 86 from an expanded configuration to a collapsed configuration (full or partial) and also to guide the distal portion 50 of the lead through the patient's vasculature system. Once collapsed, the distal portion 50 can be inserted into a patient's vasculature and guided to a stimulation site within a vessel. When the stimulation site has been reached the guiding element is removed, allowing the distal portion 50 to transition from a collapsed configuration to an expanded configuration.

According to a further embodiment of the present invention, a guide catheter is used to deliver the distal portion 50 of the lead 6 to the stimulation site within a vessel. Once inside the targeted vessel, the distal portion can be partially deployed from the guide catheter and rotated or otherwise manipulated. The electrodes located on the distal portion can be used to acutely stimulate and thus, test potential stimulation sites. Once a stimulation site has been selected using the information gained through acute stimulation, the guide catheter can be fully retracted and the distal portion deployed so as to secure and stabilize the distal portion at a stimulation site within the vessel such that stimulation can occur at the targeted stimulation site.

According to yet a further embodiment of the present invention, as shown in FIG. 6B, the distal portion 50 includes a pull wire 92. The pull wire 92 is coupled to the distal end of the lead 6, and is operable at the proximal end of the lead 6. According to one exemplary embodiment, the pull wire 92 is disposed within a lumen of the lead body 42 and is adapted to be secured at the proximal end of the lead 6. Pulling on the pull wire 92 causes the distal portion 50 including the spirals 82, 86 to further expand within the vessel, causing additional radial expansion force to be placed on the vessel walls further stabilizing the distal portion 50 of the lead 6 within the vessel. When the distal portion 50 has been stabilized, the pull wire 92 can be secured at the proximal end of the lead 6. Likewise, when it is desirable to reposition or remove the distal portion of the lead, the tension placed on the pull wire 92 at the proximal end can be released, thus releasing any additional expansion force placed on the vessel walls by activating the pull wire 92 causing further radial expansion of the distal portion 50. A guiding element or a combination of guiding elements then can be used to reposition and/or remove the distal portion of the lead from the vessel.

According to another embodiment of the present invention, the spirals 82, 86 are variably expandable. That is, the spirals 82, 86 are adapted to expand with and adapt to the natural changes in the size and diameter of the vessel while at the same time engaging and maintaining a frictional force on the vessel walls. For example, when in the internal jugular vein, the internal geometry (diameter and inner shape) of the internal jugular vein may change with blood flow and blood pressure. Similarly, when a patient is in an upright position, the diameter of the vessel may be smaller than when the patient is lying down or is in a prone position. The spirals 82, 86 account for the difference in vessel diameter by expanding so as to maintain a frictional force on the vessel walls securing and stabilizing the distal portion 50 in the vessel.

Figure 7A:
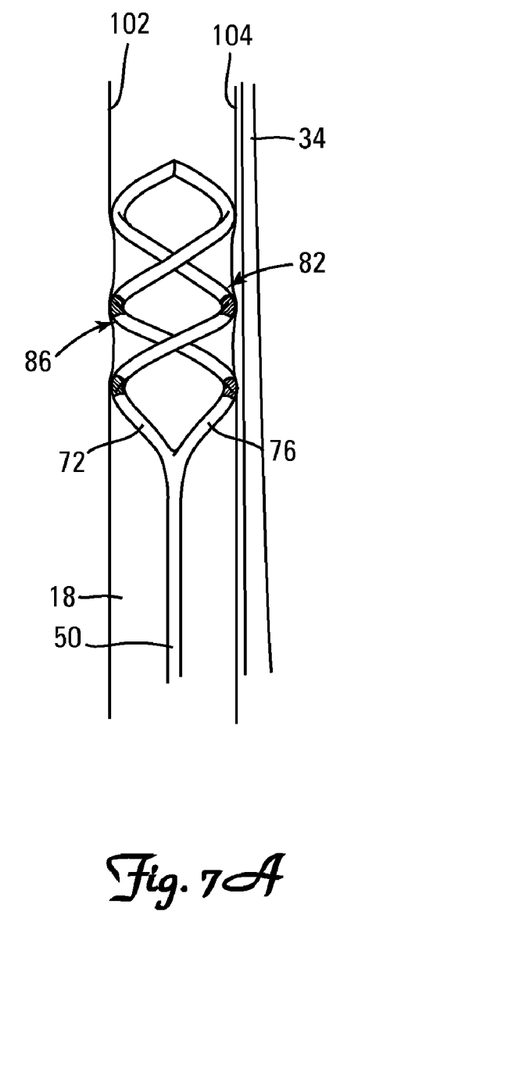
FIG. 7A is a close-up schematic view of a distal portion of a lead deployed in a vessel according to an embodiment of the present invention.
Figure 7B:
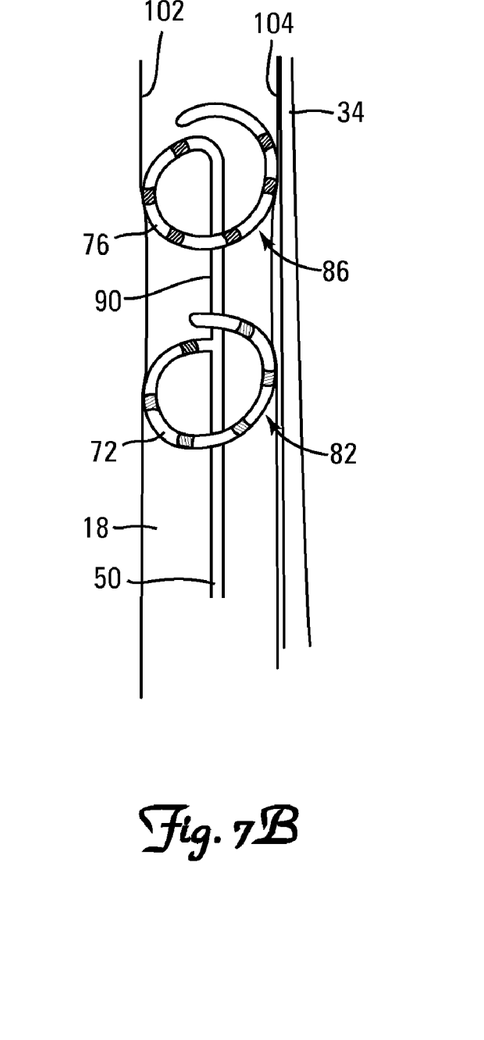
FIG. 7B is a close-up schematic view of a distal portion of a lead deployed in a vessel according to an embodiment of the present invention.

FIGS. 7A and 7B are close-up schematic views of a distal portion 50 of a lead 6 deployed within the right internal jugular vein 18 adjacent the right vagus nerve 34. Upon deployment in a patient's vasculature, the spirals 82, 86 are adapted to radially expand such that they contact and frictionally engage an inner surface of vessel walls 102, 104 securing and stabilizing the distal portion 50 of the lead 6 at a stimulation site within the vessel. The stimulation site can be described as the location within a vessel adjacent a nerve or muscle which maximizes electrical stimulation to the nerve or muscle across a vessel wall. According to an embodiment of the present invention, the spirals 82, 86 place enough radial expansion force on the vessel walls 102, 104 such that the turns of the spiral migrate outside of the original boundaries of the vessel walls 102, 104 and towards the nerve 34 to be stimulated without damaging the vessel walls 102, 104. As a result, any electrodes 66 located on the spirals 82, 86 are placed in closer proximity to the nerve 34. In one exemplary embodiment, the electrode 66 is disposed at a distance of less than 2 mm from the nerve 34 to be stimulated. In another exemplary embodiment of the present invention, the spirals 82, 86 force the vessel walls 102, 104 into direct contact with the nerve 34.

The migration of the spiral outside of the original boundaries of the vessel walls causes no damage to the vessel walls nor does the spiral erode through the vessel walls. A sheath of tissue forms over the spiral over an extended period of time such that it becomes encapsulated within the vessel walls. The outer geometry of the vessel is altered such that the outline of the spiral located within the vessel is visible.

As shown in FIGS. 1-7B, the lead 6 includes one or more electrodes 66. According to an embodiment of the present invention, one or more electrodes 66 are located on one or both spirals 82, 86. According to another embodiment, of the present invention, one or more electrodes 66 are located on one or both spirals and/or the generally straight portion 90, as shown in FIG. 6E. At least one electrode 66 is adapted to deliver an electrical pulse transvascularly to the nerve or muscle to be stimulated. Additionally, according to a further embodiment of the present invention, at least one electrode 66 is a pacing or a sensing electrode. Depending upon the application and desired result, stimulation can occur between electrodes 66 located on the same spiral 82 or 86, the straight portion 90, or between electrodes 66 located on different spirals 82 or 86 and/or the straight portion 90. According to a further exemplary embodiment, as shown in FIG. 7B, the distal portion 50 is positioned within the vessel such that generally straight portion 90 is aligned in parallel along a portion of the vagus nerve 34.

According to another embodiment of the present invention, one or both spirals 82, 86 include multiple electrodes 66. The electrodes 66 can have the same or different polarity. Multiple electrodes 66 allow flexibility in the intravascular placement of the distal portion 50 of the lead 6. Not all of the electrodes 66 need to be orientated towards the adjacent nerve or muscle tissue in order for maximum stimulation across the vessel wall to occur. Likewise, the circular or elliptical cross section of the spirals 82, 86 allow the distal portion 50 of the lead 6 to be rotated within the vessel so as to ensure that at least one electrode 66 is capable of delivering sufficient electrical stimulating pulse across the vessel wall. Additionally, the electrodes 66 can be connected to multiple individual conductors through the lead body 42 allowing for them to be individually addressable. Individually addressable electrodes 66 allow for flexibility in electrode selection. It also allows for stimulation to occur between individual electrodes 66 on the same spiral 82 or 86 or different spirals 82 or 86 and/or the straight portion 90 providing for greater control over the current field and the direction of stimulation as well as allowing for multiple options for stimulation and sensing.

According to a further embodiment of the present invention, as best shown in FIGS. 6A-6E, multiple electrodes 66 are provided at an equal distance from one another along each elongate member 72, 76. Alternatively, the electrodes 66 need not have an equal spacing from one electrode 66 to another. Additionally, as shown in FIG. 6D, the electrodes 66 are located on the straight portion 90 that interrupts the spirals 82, 86, and as such can be aligned in parallel with the nerve to be stimulated. Parallel alignment of the electrodes with the adjacent nerve increases the efficacy of stimulation as the nerve is stimulated when the electrical potential changes along the nerve. The lead body 42 including the spirals 82, 86 can be rotated or otherwise manipulated such that the electrical stimulation across the vessel walls 102, 104 to the adjacent nerve is maximized. According to the embodiments shown in FIGS. 7A and 7B, as the spirals 82, 86 expand within the vessel, the electrodes 66 are pushed up against the vessel walls 102, 104, maximizing electrical transvascular stimulation. In one embodiment, the spirals 82, 86 press up against the vessel walls 102, 104 with enough radial expansion force such that the spiral 82, 86 migrates outside the original boundaries of the vessel wall bringing at least one electrode 66 in closer proximity to the adjacent nerve.

The electrodes 66 located on the lead body 42 can have any electrode configuration as is known in the art. According to one embodiment of the present invention, the electrodes 66 are ring electrodes. According to another embodiment, the electrodes 66 are partial ring electrodes. According to yet another embodiment of the present invention, the electrodes include an exposed electrode portion and an insulated electrode portion. According to this embodiment, the electrodes 66 are masked or otherwise insulated on the inner circumference of the spirals 82, 86 The exposed electrode portion is located on the outer circumference of the spiral 82, 86. Exemplary electrodes of this type are described in commonly owned and co-pending published application US 2008/0183264 entitled "ELECTRODE CONFIGURATIONS FOR TRANSVASCULAR NERVE STIMULATION,". The lead body 42 is rotated such that the exposed electrode portion is oriented towards the adjacent nerve, muscle or tissue to be stimulated. The exposed electrode portion is configured such that it is adapted to direct or focus current towards the stimulation target. The insulated electrode portion is located on the lead body 42 opposite the exposed electrode surface. The insulated electrode portion acts as a shield from the undesired stimulation of an adjacent or nearby nerve or muscle that is not the stimulation target.

The lead 6 can be further stabilized in the internal jugular vein 34 by using a suture in a distal region of the lead body 42. In one embodiment, the lead 6 is further stabilized through the wearing of a neck brace by the patient for a period of time after implantation of the lead 6. In an alternative embodiment, the lead 6 can include fixation features well known in the art, such as silicone tines or a corkscrew-shaped fixation feature (not shown) at the distal region of the lead body 42, to stabilize the lead 6 in the internal jugular vein 34. In an alternate embodiment the fixation features can be located on one or both of the spirals 82, 86. In other embodiments, the fixation feature can be located at a distal end 56 of the lead 6. The lead 6 can also include an area on the lead body 42 that promotes tissue in-growth. In one embodiment, the area includes a roughened polymer surface on the lead body 42. In alternative embodiments, the area includes a region of stepped or inset diameter within the lead body 42, within an electrode, or between the lead body 42 and an electrode. In other embodiments, the area includes a polymer mesh, for example, a Dacron mesh, a metal mesh, for example, a stainless steel or nitinol mesh, or a bio-absorbable mesh. Examples of a bio-absorbable mesh include polyglycolic acid, poly-lactic acid, and polydioxanone. The lead 6 can include any combination of sutures, fixation devices, tissue in-growth areas, or a neck brace to improve its stability within the internal jugular vein 34.

The lead 6, according to various embodiments of the present invention, can be delivered to a stimulation site within a vessel adjacent a nerve, muscle, or tissue to be stimulated using standard techniques. According to one embodiment of the present invention, the lead 6 can be inserted in a patient's vasculature system via percutaneous stick directly into a patient's internal jugular vein to deliver therapy to the vagus nerve. According to another embodiment of the present invention, the distal portion 50 of the lead 6 is transitioned to a collapsed configuration and advanced through a patient's vasculature and delivered to a stimulation site using a guiding element such as a guide catheter. Once the site has been reached and the guide catheter is retracted, the spirals located at the distal portion 50 of the lead 6 transition from their collapsed configuration to their expanded configuration contacting and frictionally engaging the vessel walls of the vessel in which it is deployed. Likewise, a stylet or one or more guidewires may be inserted into the lead lumen and/or a lumen located within one of the elongate members 72 or 76 to straighten the distal portion 50 from its predetermined spiral shape. The distal portion is then guided through the vasculature to a stimulation site located within a vessel.

Once a stimulation site has been reached, the guidewire or stylet is removed allowing the distal portion 50 of the lead 6 to return to its predetermined shape. Pull wires can also be used to further expand the spirals in a vessel such that they place an additional radial force on the wall further securing and stabilizing the distal portion 50 within the vessel. Whatever the delivery method, once the distal portion has reached a stimulation site within a vessel adjacent a nerve to be stimulated, the distal portion 50 expands, contacting and frictionally engaging the vessel walls of the vessel in which it is deployed.

The lead body 42 and, thus, the spiral members 82, 86 can be rotated within the vessel to orient the electrodes 66 towards the stimulation target. Additionally, the lead body 42 can be further rotated or positioned until a maximum or optimum electrical stimulation threshold by the electrodes 66 has been achieved across the vessel wall to the adjacent nerve or muscle to be stimulated. The stimulating pulse delivered by the electrodes can then be measured to determine if an optimal stimulation threshold has been reached. The lead 6 can be repositioned within the vessel by either rotating the lead body 42 within the vessel or reintroducing the guiding member such as the guide catheter or guidewire to collapse and/or straighten the distal portion 50 of the lead 6.

The lead 6 can then either be repositioned and/or removed from the vessel. According to a further embodiment of the present invention, the distal portion can be partially deployed from a guide catheter in order to acutely stimulate the electrodes. Once a suitable stimulation site has been identified, the guide catheter can be retracted and the distal portion 50 fully deployed within the vessel at the stimulation site.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An intravascular lead adapted to be deployed to a stimulation site within an internal jugular vein having a vessel wall adjacent a vagus nerve, the lead comprising:

a lead body including a proximal end adapted to be connected to a pulse generator and a bifurcated distal portion for securing and stabilizing the lead in the vessel, the bifurcated distal portion comprising at least one bifurcation point and a first elongated member and a second elongated member, the first and second elongated members branching away and extending distally from the at least one bifurcation point, the first elongated member forming a first spiral and the second elongated member forming a second spiral, wherein the first and second spirals are congruent, anti-parallel spirals having a same longitudinal axis forming a double helix and wherein the spirals are adapted to transition from a collapsed configuration for inserting the lead through a patient's vasculature system to an expanded configuration, wherein in the expanded configuration the spirals have a predetermined effective outer diameter ranging from about 5 to about 50% greater than the inner diameter of the internal jugular vein and are adapted to frictionally engage the vessel wall of the vessel in which the distal portion is deployed so as to impart a lateral force on the vessel wall to urge the vessel wall in a direction towards the vagus nerve;

a plurality of conductors extending within the lead body from the proximal end to the distal end;

a plurality of electrodes adapted to deliver an electrical pulse transvascularly to the nerve located on the distal portion, each individual electrode comprising a masked portion and an unmasked portion and coupled to an individual conductor such that each electrode is individually addressable, wherein when the distal portion is expanded, the unmasked portion of at least one electrode is located on an outer circumference of at least one spiral and is adapted to be oriented in a direction towards the vagus nerve and the masked portion is located on an inner circumference of the at least one spiral and is adapted to be oriented away from the vagus nerve.

2. The intravascular lead according to claim 1, wherein at least a first electrode is located on the first spiral and at least a second electrode is located on the second spiral.

3. The intravascular lead according to claim 1, wherein the spirals have an outer effective diameter ranging from about 5 percent to about 20 percent greater than an inner diameter of the internal jugular vein in which the distal portion is deployed.

4. The intravascular lead according to claim 1, wherein when the distal portion is expanded the unmasked portions of at least two electrodes are oriented in a direction towards and are adapted to be aligned with the vagus nerve.

5. The intravascular lead according to claim 1, wherein upon implantation in the vessel, the distal portion is in the expanded configuration and is adapted to urge the vessel wall in a direction towards the vagus nerve so that a distance between one or more electrodes and the vagus nerve is less than 2 mm.

6. The intravascular lead according to claim 1, wherein the distal portion comprises a superelastic material selected from the group consisting of Nitinol and MP35N.

7. The intravascular lead according to claim 1, further comprising a pull wire attached to a distal end of the lead.

8. An intravascular lead adapted to be deployed to a stimulation site within an internal jugular vein having a vessel wall adjacent a vagus nerve, the lead comprising:
a lead body including a proximal end adapted to be connected to a pulse generator and a bifurcated distal portion, the bifurcated distal portion comprising at least one bifurcation point, a first elongated member forming a first spiral, a second elongated member forming a second spiral, wherein the first and second elongated members branch away and extend distally from the at least one bifurcation point, and a generally straight portion occurring between the first spiral and the second spiral, wherein each of the first and second spirals have a predetermined effective outer diameter ranging from about 5 to about 50% greater than the inner diameter of the internal jugular vein and are adapted to expand so as to impart a lateral force on the vessel wall to urge the vessel wall in a direction towards the vagus nerve and to secure and stabilize the distal portion within the vessel;
a plurality of conductors extending within the lead body from the proximal end to the distal end; and
at least a first electrode located on the first spiral and at least a second electrode located on the second spiral, each of the first and second electrodes coupled to an individual conductor extending within the lead body and adapted to deliver an electrical pulse transvascularly to the vagus nerve and each electrode comprising a masked portion and an unmasked portion, wherein when the distal portion is expanded, the unmasked portion of at least the first electrode is located on an outer circumference of the first spiral and is adapted to be oriented in a direction towards the vagus nerve and the masked portion is located on an inner circumference of the first spiral and is adapted to be oriented away from the vagus nerve.

9. The intravascular lead according to claim 8, wherein the second elongated member comprises a super-elastic wire.

10. The intravascular lead according to claim 8, wherein the first and second electrodes are in alignment with each other such that they are adapted to be aligned in parallel with the nerve to be stimulated.

11. The intravascular lead according to claim 8, wherein the first spiral is in serial alignment with the second spiral.

12. The intravascular lead according to claim 8, wherein the spirals are configured to expand and frictionally engage at least one vessel wall upon deployment in a vessel.

13. The intravascular lead according to claim 8, wherein the distal portion comprises a superelastic material selected from the group consisting of Nitinol and MP35N.

14. The lead according to claim 8, further comprising at least one electrode located on the generally straight portion.

15. A method of providing an electrical stimulus therapy to a nerve from an adjacent vessel, the method comprising:
advancing an intravascular medical lead into a vessel located adjacent to a nerve to be stimulated, the intravascular medical lead including a lead body comprising: a proximal end connected to a pulse generator; a bifurcated distal portion, the bifurcated distal portion comprising at least one bifurcation point and a first elongated member forming a first spiral and a second elongated member forming a second spiral, the first and second elongated members branching away and extending distally from the at least one bifurcation point; at least one conductor extending with the lead body; and at least one electrode located on at least one spiral of the distal portion and operatively coupled to the at least one conductor, wherein the at least one electrode is adapted to deliver an electrical pulse transvascularly to the nerve, the at least one electrode comprising a masked portion and an unmasked portion wherein when the distal portion is expanded, the unmasked portion of the at least one electrode is located on an outer circumference of the at least one spiral and the masked portion is located on an inner circumference of the at least one spiral;
transitioning the distal portion of the lead body from an expanded configuration to a collapsed configuration;
delivering the distal portion of the lead body to a stimulation site located within the adjacent vessel;
rotating the distal portion of the lead body to orient the unmasked portion of the at least one electrode located on the at least one spiral in a direction towards the nerve to be stimulated;
detecting an optimal stimulation threshold for stimulating the nerve;
expanding the distal portion to secure and stabilize the lead within the vessel; and
electrically stimulating the adjacent nerve from a location within the vessel while simultaneously shielding adjacent nerves or muscles that are not the stimulation target from undesired stimulation.

16. The method according to claim 15, further comprising repositioning the lead.

17. The method according to claim 15, wherein the adjacent vessel is the internal jugular vein and the nerve is the vagus nerve.

18. The method according to claim 15, wherein the adjacent vessel is the brachiocephalic vein and the nerve is the vagus nerve.

19. The method according to claim 15, wherein the adjacent vessel is the superior vena cava and the nerve is the vagus nerve.

20. The method according to claim 15, further comprising the step of pulling on a pull wire attached to a distal end of the lead body to further expand the distal portion in the vessel in which it is deployed.

21. The method according to claim 15, wherein the step of transitioning the distal portion from the expanded configuration to the collapsed configuration comprises inserting a stylet into a lumen provided in the lead body to collapse the distal portion of the lead.

22. The method according to claim 15, wherein the step of transitioning the distal portion of the lead body from the expanded configuration to the collapsed configuration comprises advancing the distal portion of the lead through a guide catheter configured to retain the distal portion in a collapsed configuration.

23. The method according to claim 22, further comprising retracting the catheter to at least partially expand the distal portion.

24. The method according to claim 15, further comprising aligning two or more electrodes located on the distal portion in parallel with the nerve.

* * * * *